(12) United States Patent
O'Neill

(10) Patent No.: US 8,292,839 B2
(45) Date of Patent: Oct. 23, 2012

(54) RECIRCULATION SWITCH FOR BLOOD CARDIOPLEGIA

(76) Inventor: William G. O'Neill, Maple Grove, MN (US)

( * ) Notice: Subject to any disclaimer, the term of this patent is extended or adjusted under 35 U.S.C. 154(b) by 501 days.

(21) Appl. No.: 12/384,786

(22) Filed: Apr. 9, 2009

(65) Prior Publication Data
US 2010/0262063 A1    Oct. 14, 2010

Related U.S. Application Data

(60) Provisional application No. 61/123,401, filed on Apr. 9, 2008.

(51) Int. Cl.
*A61M 37/00* (2006.01)
*A61M 1/00* (2006.01)

(52) U.S. Cl. ........... 604/6.14; 604/5.01; 604/6.07; 604/6.11; 604/6.13; 422/44; 422/45; 422/46; 422/47; 422/48

(58) Field of Classification Search .......... 604/4.01, 604/6.11, 7, 27, 500, 5.01, 6.07, 6.13, 6.14; 422/44, 45, 46, 47, 48
See application file for complete search history.

(56) References Cited

U.S. PATENT DOCUMENTS

| | | | | |
|---|---|---|---|---|
| 3,776,249 A * | 12/1973 | Wailes et al. | ................... | 137/14 |
| 4,249,923 A * | 2/1981 | Walda | .............. | 62/394 |
| 4,425,113 A * | 1/1984 | Bilstad | ................ | 604/6.04 |
| 4,425,116 A * | 1/1984 | Bilstad et al. | ................ | 604/34 |
| 4,512,163 A * | 4/1985 | Wells et al. | ................ | 62/394 |
| 4,874,359 A * | 10/1989 | White et al. | ................ | 604/6.09 |
| 5,195,960 A * | 3/1993 | Hossain et al. | ................ | 604/34 |
| 5,358,481 A * | 10/1994 | Todd et al. | ................ | 604/6.1 |
| 5,385,540 A * | 1/1995 | Abbott et al. | ............... | 604/6.13 |
| 5,403,281 A * | 4/1995 | O'Neill et al. | ............... | 604/113 |
| 5,464,388 A * | 11/1995 | Merte et al. | ................ | 604/153 |
| 6,071,258 A * | 6/2000 | Dalke et al. | ................ | 604/5.01 |
| 2006/0015056 A1 * | 1/2006 | Ellingboe et al. | ............ | 604/6.11 |

* cited by examiner

*Primary Examiner* — Tatyana Zalukaeva
*Assistant Examiner* — Adam Marcetich
(74) *Attorney, Agent, or Firm* — Patterson Thuente Christensen Pedersen, P.A.

(57) ABSTRACT

A switch comprises a rotating switch member which provides fluid communication in three modes; infusion, recirculation and priming The switch is located between the oxygenator and drug bag and the cardioplegia pump raceway. The switch has three channels molded into the rotating manifold which either direct blood and cardioplegia into the coronary arteries of the patient or into a recirculation line. When the switch is rotated into the recirculation line, a hose is in fluid connection through the switch and connects the recirculation line with the pump blood and drug inlet lines thereby allowing cooling of the cardioplegic mixture during the time between infusions.

5 Claims, 8 Drawing Sheets

RECIRCULATION SWITCH FOR BLOOD CARDIOPLEGIA

CROSS-REFERENCE TO RELATED APPLICATIONS

This application claims the benefit of Provisional Patent Application Ser. No. 61/123,401 entitled, "Recirculation Switch for Blood Cardioplegia," filed Apr. 9, 2008.

BACKGROUND

The present invention is an improved cardioplegia delivery system for arresting the heart during cardiopulmonary bypass. During the cardiopulmonary bypass procedure, the patient's heart and lungs are supported by the cardiopulmonary bypass (CPB) machine (heart lung machine). It is necessary in many cases and desirable in some cases to completely arrest the beating of the heart in order to perform the heart surgery. For example a valve replacement surgery nearly always requires cessation of the beating heart since the heart chambers must be opened and the surgeon requires a clear, non-bloody field in which to work. During most coronary artery bypass graft (CABG) procedures, the surgeon may elect to arrest the heart and place the patient on the CPB machine in order to suture to a still, blood free coronary artery. This case is considered optional because some CABG's are done without arresting the heart but by stabilizing and immobilizing a portion of the heart upon which the surgeon desires to operate.

Cardioplegia is a common technique in cardiopulmonary bypass. Cardioplegia is a cold solution which is injected into the patient's coronary arteries. A key, active component of cardioplegia is potassium. The combination of potassium and cold (typically <10° C.) arrests the heart. The cardioplegia is typically injected in bolus' of approximately 200-400 cc. of fluid approximately every 15-20 minutes. A majority of surgeons elect to mix oxygenated blood from the heart lung machine into the cardioplegia and cool the mixture. The blood acts to nourish and oxygenate the patient's heart muscle or myocardium.

The current state of the art of myocardial protection which is another term for cardioplegia delivery, is to deliver the blood and drug either via two separately controllable roller pumps or via two tubes in the same roller pump raceway. A peristaltic roller pump is a positive displacement pump. It will displace a volume dictated by the relative volume of the tubing in the pump raceway. The volume of the tube in the raceway is defined by the equation:

$$V = L*(\pi*d^2/4) \quad \text{eqn. 1}$$

Where:
L=length of tubing in the pump raceway
π=pi
d=inner diameter of the plastic tubing A majority of operations are done each year with cardioplegia delivered by the two tubes in a single raceway of a roller pump. It is the surgeons preference as to what ratio of blood and drug are mixed together. Less frequently, a dual head roller pump may be used to deliver the cardioplegic solution. In the case of two pump heads, the pumps can run at different rates and variable blood to drug ratios can be delivered. In the former case of a single pump raceway, the ratio of the two tubes determines the delivered mixture of blood vs. cardioplegic drug. For example, a popular ratio is four parts blood to one part drug. This is accomplished by a 0.25" i.d. tube for the drug and a 0.125 inch i.d. tube for the drug. The ratio of the two volumes for a given identical length of tubing is four.

The conventional state of the art is there are multiple tubing sets sold with various blood to drug ratios. Popular options include 4:1 blood to drug, 2:1, 1:1, 8:1, etc. If multiple surgeons in the same hospital desire different myocardial protection protocols, the hospital must stock different part numbers.

The conventional state of the art in cardioplegia delivery involves cooling the mixture with a blood to water heat exchanger. Blood cardioplegia is pumped on one side of the heat exchanger while icy cold water is pumped on the other side of the heat exchanger. Heat is transferred from the blood into the water which cools the blood/drug mixture to a hypothermic temperature of 4-10° C.

Cardioplegia is typically delivered intermittently. For example, at the beginning of the bypass surgery, the surgeon may elect to arrest the heart with a large bolus of cardioplegia; for example 500-1,000 ml. Once the heart is arrested, it is desirable to turn off the cardioplegia so that blood does not continue to circulate through the patient's coronary arteries. As the surgeon is repairing a valve or sewing a bypass graft into a coronary artery, blood in the coronary arteries will diminish visualization of the surgical site. Since the cold, arrested heart requires much less oxygen and nutrients, the heart can stay dormant for 15-25 minutes between doses of cardioplegia with minimal ill effects. Typically a lower dose of cardioplegia is delivered every 10-20 minutes and the pump is turned off in between doses. Maintenance doses of cardioplegia after the initial arrest will range from 200-400 ml.

At the end of the surgery, the heart is typically warmed. A warm dose of cardioplegia is frequently given to transition the myocardial tissue from a cold, dormant state to warm and beating. Thus the cardioplegia delivery system should optimally both cool and warm the blood. This can be done by pumping either cold or warm water through the water to blood heat exchanger.

Another present convention in cardiopulmonary bypass equipment is to locate the heart lung machine remotely from the patient. Typically the patient's venous blood is drained from the venous side via large bore catheters inserted in the patient's right atrium and inferior vena cava. The blood is drained through approximately eight feet of plastic tubing (typically polyvinyl chloride or PVC) to the venous reservoir which collects the blood. Blood is pumped via either a roller pump or a centrifugal pump through an arterial heat exchanger which is used to cool the patient's systemic temperature. Blood passes out of the heat exchanger into the oxygenator which blows off carbon dioxide and adds oxygen to the blood. Blood exits the oxygenator/heat exchanger into eight feet of tubing to return blood to the patient's aorta.

DISADVANTAGES OF THE CURRENT ART

There are multiple disadvantages of the conventional cardioplegia systems. Those disadvantages include the high priming volume of the cardioplegia tubing sets, the "dead volume" of cardioplegia which warms in between doses of drugs, and the need to cool the blood with ice water which contains toxic chemicals.

High priming volume is problematic because it dilutes the patient's blood (hemodilution). If there are fewer red blood cells in the cardiopulmonary bypass circuit as a percentage of the total volume, less oxygen can be delivered per pump rotation and less carbon dioxide may be removed.

A second problem with cardioplegia circuits is the 'dead volume" downstream of the cardioplegia heat exchanger. As discussed in the previous section, typically cardioplegia is administered intermittently every 10-20 minutes. The blood in the tubing downstream of the heat exchanger will begin to be warmed by the ambient temperature surrounding the bubble trap and tubing line. A bubble trap is typically inserted downstream of the heat exchanger to catch air bubbles prior to being delivered to the patient. The "dead volume" of the combined bubble trap and the delivery tube may range from 70 to 150 ml. of cardioplegic volume. FIG. 7 illustrates the temperature of the solution at the cardioplegia cannula entering the heart during multiple intermittent doses of cardioplegia. Referring to FIG. 7, when the pump is turned on, the blood to water heat exchanger cools the solution and the temperature of the fluid flowing into the heart begins to cool. Once the pump is turned off however, the blood in the tubing begins to rewarm due to ambient conductive warming through the walls of the bubble trap and tubing. If, for example, the 70-150 ml. warms to 15 degrees in the twenty minutes between infusions, and a typical maintenance dose of 250 ml. is delivered, as much as one third to one half of the dose is delivered at a much warmer temperature than desired. This means more drug must be added to arrest the heart which again leads to hemodilution and the time to deliver the cardioplegia is increased.

Several devices have tried to overcome the problem of warming of the cardioplegia in between doses. All have drawbacks compared to the invention described in this document. O'Neill described in U.S. Pat. No. 5,403,281 an in line delivery heat exchanger. In this invention, the heat exchanger is a flexible tube surrounded by a water line. The heat exchanger is in essence the delivery line and the dead space is reduced to only a few milliliters of blood in the several inches between the end of the delivery line heat exchanger. The disadvantage with this device is that the toxic water pumped from the cooler heater would circulate virtually up to the patient's heart. Any slight leak might squirt water into the sterile field. If an open cavity was exposed to this non-sterile, bacteria ridden water, the patient would be at serious risk of infection.

Another problem with this invention is the poor conductivity of flexible, plastic materials which are typically used in delivery lines. Delivery lines must be flexible to snake from the pump, around the surgeon, and up close to the patient's heart. Flexible materials like rubber or plastics, have much poorer thermal conductivity than stainless steel or aluminum which are more traditionally used in blood to water heat exchangers. These materials require more surface area and prime volume to achieve the same heat exchanger performance.

Sarns/3M Health Care sold a cardioplegia delivery system with blood recirculation capability in the late 1970's and 1980's. The device was referred to as the Integrated Cardioplegia Delivery System (ICDS). The invention is described in U.S. Pat. Nos. 4,512,163, 4,433,971 and 4,427,009. The ICDS combined a hardware pump and cooler heater with a disposable tubing set. The ICDS allowed recirculation of the blood and drug solution by rotating a mechanical, lever operated valve which was part of the hardware. The ICDS system also had two eight foot tubes connecting the cardioplegia non-sterile circuit with the patient. One of the two delivery lines would deliver cardioplegia while a second would recirculates fluid to a cardiotomy reservoir. The cardiotomy reservoir is a filter container in which suction blood was filtered prior to returning to the bypass circuit. In one switch position, the blood and cardioplegia fluids would flow through two open PVC tubes. During recirculation the lever switch would close the tubing coming from the drug source and open a second blood tube connected to the oxygenator. This second lever position would have both pump tubes always pulling fluid from an external source. The lever was designed to prevent an occluded drug tube from generating high negative pressures in the pump head. When recirculation of the system was desired, the perfusionist would rotate the lever to "recirculation" mode and simultaneously the surgeon would move a clamp from the recirculation line to a short piece of tubing connected to the cardioplegia cannula. This system was sold for several years but was discontinued due to the high cost of the reusable cardioplegia hardware. The expensive, reusable hardware was redundant with equipment often already present in most operating rooms. For example, the pump technicians had roller pumps included in the heart lunch machines. The pump technicians also had separate cooling sources such as a Sarns Cooler/Heater. The recirculation circuit required the coordination of both the surgeon and the perfusionist. When recirculation was desired, the perfusionist would rotate the lever plus the surgeon would move a clamp from one tube to another. If the surgeon occluded the wrong tube, the circuit might overpressurize. If the surgeon did not move the clamp, blood would continue to pump into the coronary arteries. Finally the heat exchanger was highly inefficient, being made from plastic tubing. It required a high priming volume. For all of these reasons, the ICDS was discontinued and no longer sold in the early 1980's.

DLP introduced a cardioplegia recirculation switch in the 1980's. Called the ARISS Perfusion switch, the devices can be found on the on line DLP catalog under product codes 13000. 13004. and 13051. The device alternated between pinching closed one of two plastic tubes close to the patient's coronary arteries. When the recirculation tubing was occluded, the cardioplegia solution would flow directly into the patient heart. By occluding the delivery line and opening the recirculation tube, fluid would stop flowing to the heart and flow back and would drain into the cardiotomy reservoir. Because the pump tubes are typically connected directly to the blood source (oxygenator) and the drug source, it was not possible to recirculate the cardioplegia solution through the pump head. The DLP switch had the disadvantage of continuously diverting the blood/cardioplegia mixture into the cardiotomy reservoir. Once sufficient blood was collected in the cardiotomy, the blood was returned to the patient. This returned blood would dilute the blood and increase the problem of hemodilution. Thus hemodilution is a drawback to using this product and the benefit of quick cooling had to be weighed against the drawback of hemodilution.

Merte et al. in U.S. Pat. No. 5,464,388 disclosed a mechanical valving system which could allow recirculation of the blood. In this device, only one pump line goes through the pump raceway. Three plastic tubing feed into the pump line; blood line, cardioplegia line and recirculation line. Three solenoid valves pinch off the three tubes according to a computer control. During the administration of cardioplegia, the pump is turned on and the solenoid valves occluding the blood and cardioplegia tubes are alternately opened and closed. Only one of the two valve would be open at any one time. Thus the ratio of blood and drug could be controlled by controlling the ratio of the opening of the two valves. During recirculation mode in between infusions of cardioplegia, both blood and cardioplegia valves are closed and the recirculation line is opened. The delivery line and recirculation lines would both be eight feet in length with a "Y" connector a the distal end immediately proximal to the patient's heart.

The mechanical device described in Merte was never commercialized probably due to the problem of adding expensive hardware to solve the problem of varying blood to drug ratios and recirculating of dormant fluids. The hardware solution adds cost and complexity to a relatively simple cardioplegia delivery system.

Leonard in U.S. Pat. No. 4,883,455 discloses a recirculation line which was controlled by a pressure relief valve in a recirculation line. The cardioplegia solution is pumped to the patient. A "Y" just before the cardioplegia enters the heart muscle permits blood to flow either into the heart or back down a recirculation line. Within the recirculation line was a pressure relief check valve. The perfusionist could move a hemostat or mechanical occluder to the delivery line from the recirculation line; thereby opening up the recirculation line. This system did not recirculate and cool the blood in the delivery line because it would only recirculate fluid upstream of the clamp. In order to recirculate the blood and drug in the delivery line, the perfusionist would have to coordinate the clamping of the lines with the surgeon at the table. Typically the surgeon is busy and currently does not need to be involved in turning on and off cardioplegia. This device also suffers a similar problem as the DLP device which was hemodilution of the bypass circuit. Because the valve was downstream of the pump, the recirculation line would have to discharge the blood and drug mixture back into the cardiotomy and would increase hemodilution the longer recirculation was required.

In summary no device has been designed which is an optimum blend of avoiding hemodilution without an expensive purchase of complex hardware. Since the Sarns ICDS has been discontinued by the company and the Merte and Leonard devices were never commercialized even though the patents have been issued for over fifteen years, it may be concluded that the disadvantages described truly made devices uneconomical for perfusion supply companies. The DLP device has had low sales.

Despite the multiple attempts to solve the problems associated with recirculation of blood cardioplegia, no device is in widespread use which solves the problem at the current time. All the current cardioplegia system are configured only to deliver cardioplegia. All current cardioplegia systems suffer from the warming of the blood/drug solution during intermittent infusions.

BRIEF DESCRIPTION OF THE INVENTION

The invention is cardioplegia circuit employing a novel recirculation switch. The invention recirculates the blood and drug in the delivery line and does not result in hemodilution. The device is activated by the perfusionist at the heart lung machine and does not require the intervention by the surgeon nor anone in the sterile field. Finally the device is simple and included in the disposables with no additional hardware required. Since the switch recirculates the blood and drug in the delivery line right up to the patient's heart, the invention allows for the "instant cooling" advantage This embodiment features a switch located "upstream" of the cardioplegia pump (between the blood oxygenator/cardioplegia drug bag and the pump). Refer to FIG. 1 which illustrates the complete circuit. The normal delivery mode of the switch is shown in FIG. 4. The switch features a rotating element manifold which rotates within the switch outer body. Exiting the switch are two plastic tubes which go through the raceway of the cardioplegia pump or pumps. A dual head pump may be used to vary the drug/blood ratio. Exiting the pump, the pressurized fluids are mixed at a "Y" or "tee" joint before entering the blood to water heat exchanger. Exiting the blood to water heat exchanger, the chilled, pressurized mixture travels through an eight foot long delivery line. At the distal end of the delivery line is a "Y" connector. The "Y" connector routes blood either into the patient's heart or to the recirculation line depending upon the orientation of the switch. The recirculation line is another eight foot long PVC tube which terminates in the switch body.

The outer body of the recirculation switch may be made of polycarbonate, acrylic, clear ABS, PET, nylon or any other biocompatible plastic. The switch must be weldable so certain materials weld better with radio frequency welding versus ultrasonic welding. When the switch is in the "Delivery" position as shown in FIG. 4, the pump pulls blood and drug through two channels (26 and 28) molded into the rotating manifold. In this position, the channels connect the blood and drug inlet lines with the two plastic tubes (23 and 24) which enter pump (17). Blood and drug travel through the circuit and are injected into the patient's heart; cooling and preserving the heart muscle.

The pump technician or perfusionist would activate recirculation mode by rotating the manifold of the switch approximately 90 degrees. This embodiment is shown in FIG. 5. In this embodiment, the pump tubing are now in direct fluid communication with the recirculation line. Both pump lines (e.g. ¼" i.d. blood and ⅛" i.d. drug) are supplied by the manifold. This is important since a completely occluded pump tube will create high negative pressure which is damaging to the red blood cells. In this switch position, the blood and drug sources are disconnected from fluid communication with the pump. Therefore only the fluid in the recirculation line can be pulled into the pump and no fluid is injected into the heart. This allows the solution to be cooled during the intermittent time between desired cardioplegia infusions.

FIG. 6 is a graphical representation of the temperature entering the patient's heart from a conventional cardioplegia circuit compared to the temperature of fluid exiting the "Recirculation" circuit described in this invention. (D0020-003 rev. A: "Solution Temperature-Conventional vs. Recirculation"). This graph is taken from actual laboratory measurements of the outlet solution temperatures of two cardioplegia systems. In FIG. 6, both fluid sources in the delivery line start at approximately ambient temperature (20° C.). The temperature of the solution exiting the circuit "Cardioplegia with recirculation" drops to about 2-3° C., within 5-10 seconds. The temperature of the solution in the conventional circuit starts to drop much more gradually. The temperature of the solution exiting this cardioplegia set does not go below 5° C. for 60 seconds. This is caused by the volume of the fluid in the delivery line and bubble trap which have warmed to ambient temperature in the twenty minutes between administrating doses of cardioplegia. In contrast, the fluid in the delivery line in the present invention is slowly pumped up to the patient's heart and back through the heat exchanger. This keeps the solution at a temperature very close to the inlet water temperature. Once the perfusionist or pump technician rotates the switch from "Recirculation" to "Delivery" mode, all of that cold solution in the delivery line and bubble trap flows virtually immediately into the patient's heart.

This embodiment offers several advantages over the prior art. Unlike the DLP Medtronic blood recirculation and unlike Leonard, the recirculation mixture does not empty into the cardiotomy and increase hemodilution. Unlike O'Neill, the device does not pose the additional risk of circulation nonsterile water near the patient. And unlike Merte and Wells, no expensive major capital equipment purchase is required.

Unlike conventional cardioplegia sets, this delivery device should arrest the heart more quickly. This should speed the procedure and potential allow the pump technician to deliver less cardioplegia. If less cardioplegia is delivered, the improved cardioplegia circuit will minimize hemodilution since less drug solution will travel through the heart into the rest of the cardiopulmonary circuit.

The invention has applications outside of cardiac surgery. The invention permits remote switching of a fluid which may require recirculation or mixing. For example, during a minimally invasive procedure, it may be desirous to recirculates a fluid down into a small diameter delivery device and then remotely "Switch on" delivery of the fluid. For example, some medical adhesives and sealants such as medical grade cyanoacrylates require mixing of the monomer with a second initiator component which starts the polymerization process. It may be desirous to pump the glue through a recirculation tube to thoroughly mix the glue and initiator. Then when the glue and initiator are thoroughly mixed, the surgeon may rotate a switch and allow the mixture to be delivered to the surgical site. This invention could permit an activation switch to be located outside of the small diameter cannula and allow small diameter tubes to circulate the fluid through the cannula. Using the invention as a remote switching mechanism may only require one supply source and only two internal fluid channels in the manifold.

DETAILED DESCRIPTION

Figure 1:
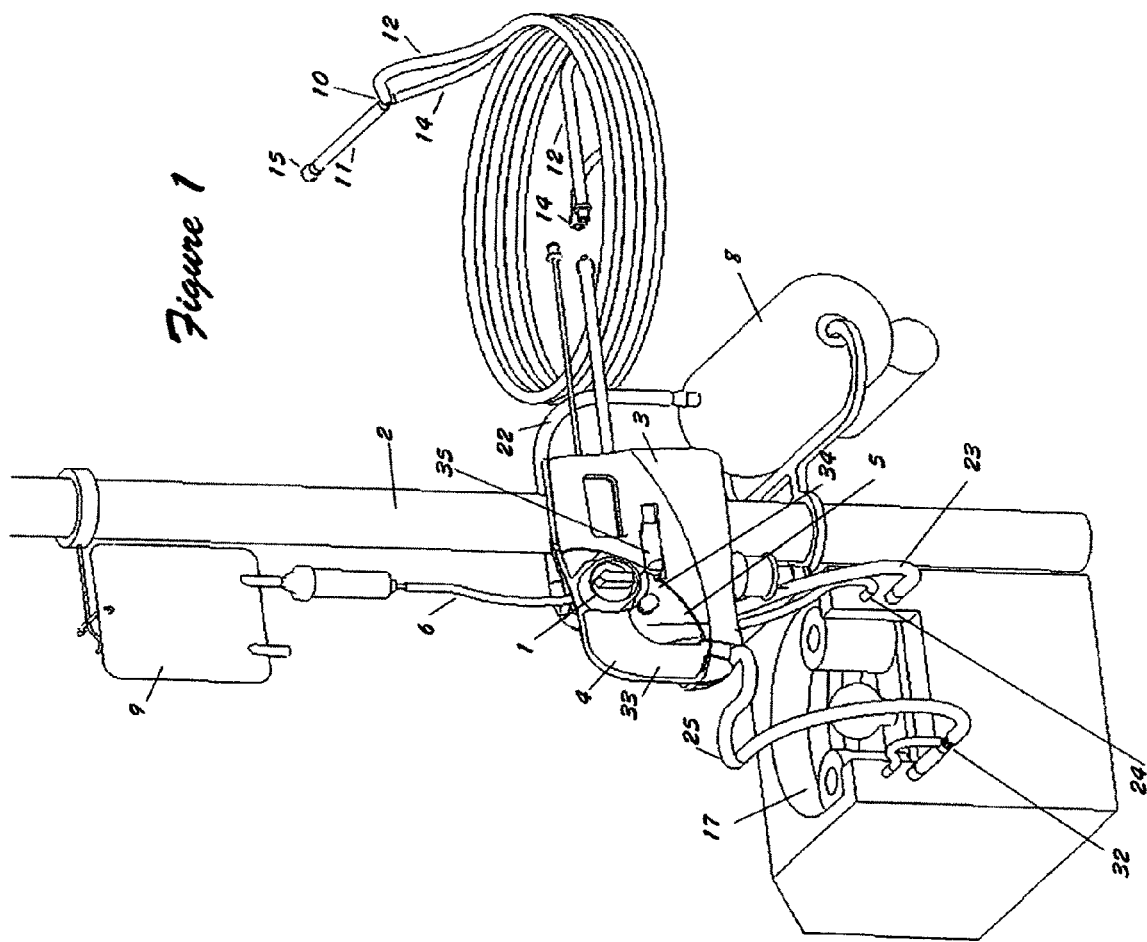
FIG. 1 illustrates the cardioplegia delivery cartridge in the reusable bracket.

A proposed design of the cardioplegia system that incorporates the disposable recirculation switch is shown in FIG. 1. The disposable cartridge (4) mates with the reusable bracket (3). The disposable cartridge (4) includes a blood to water heat exchanger (5), a bubble trap (34) a pressure manometer (33) and the recirculation switch (1). The bracket mounts to a conventional pole (2) which is common on heart lung machines. The cartridge mating to the bracket design is optimized for easy set up and priming for the perfusionist. The perfusionist simply slides the disposable cartridge (4) into the reusable bracket (3) and four connections are automatically made; two water lines, the pressure manometer and the temperature sensor. The temperature sensor (35) is built into the reusable bracket and is spring loaded. The spring forces firm contact between the thermistor sensor and the outside of the bubble trap housing (34). By putting the temperature sensor into the bracket, the disposable can eliminate an expensive thermistor coupling well. For example Qosina offers temperature sensors which mate to luer adapeters. Qosina models 27206 and 27207 are off the shelf monitoring ports for these applications. These items are priced in excess of $3 and can be eliminated with a dedicated surface probe which mates with the bubble trap. Building the sensor into the dedicated bracket can be done relatively inexpensively. A battery powered thermistor sensor can be purchased from for roughly $80 and built into the hardware. For example Omega.com offers a hand held, battery operated thermometer (model HH11A) for $65.

The recirculation switch (1) is designed to operate in three modes; infusion, recirculation and priming. Referring to FIG. 1, blood and drug are pumped from the oxygenator (8) and drug bag (9) respectively. Both fluids are plumbed to the recirculation switch (1) using flexible plastic tubing (items 6 and 22). Blood passes through the switch into a flexible plastic tube (23) which is placed into the raceway of the roller pump (17). Likewise the cardioplegic drug flows through the switch into tubing (24) which is also routed through the roller pump (17). The cross sectional area of the blood (23) and drug tubes (24) will dictate the ratio of unit of drug to a unit of blood. Upon exiting the roller pump, the pressurized blood and drug are combined in a tee connector (36) and then the mixture passes into another flexible tube (25). The blood and drug mixture are then pumped from tube (25) into the cartridge (4).

Inside the cartridge, the fluid flows through a water to blood heat exchanger (5) into a bubble trap (34). A pressure manometer (33) is built into the disposable and is used to monitor the pressure of the blood drug solution. The blood/drug mixture flows through the heat exchanger and bubble trap and exits into the delivery line (12).

The delivery line (12) is approximately eight feet of flexible plastic tubing with an inner diameter of 0.188 inches. Eight feet of distance is required to separate the sterile components at the patient from the non-sterile area at the heart lung machine. At the distal end of the delivery line (12), is a "Y" connector (10). Attached to the other two legs of the "Y" connector (10), are a short infusion line (11) and another long flexible tube (14) which is the recirculation hose. The infusion line (11) terminates in a standard male luer connector (15) which will mate with female luer connectors which are standard on cardioplegia cannula. The cardioplegia cannula is inserted into the patient's heart.

The other eight foot tube is the recirculation line (14). This tube is of smaller diameter (0.125 inch inner diameter) and routes the mixture back to the switch when the switch (1) is rotated into the "Recirculation" position. Tubing is of smaller diameter to minimize the priming volume of the circuit. When the blood/drug mixture is recirculating, the pump technician will be instructed to decrease the pump flow rate. By pumping slowly through the recirculation line, the fluid will remain chilled by the heat exchanger but blood will not be damaged by shear stresses imposed by high flow rates in a small diameter tubing.

Figure 2:
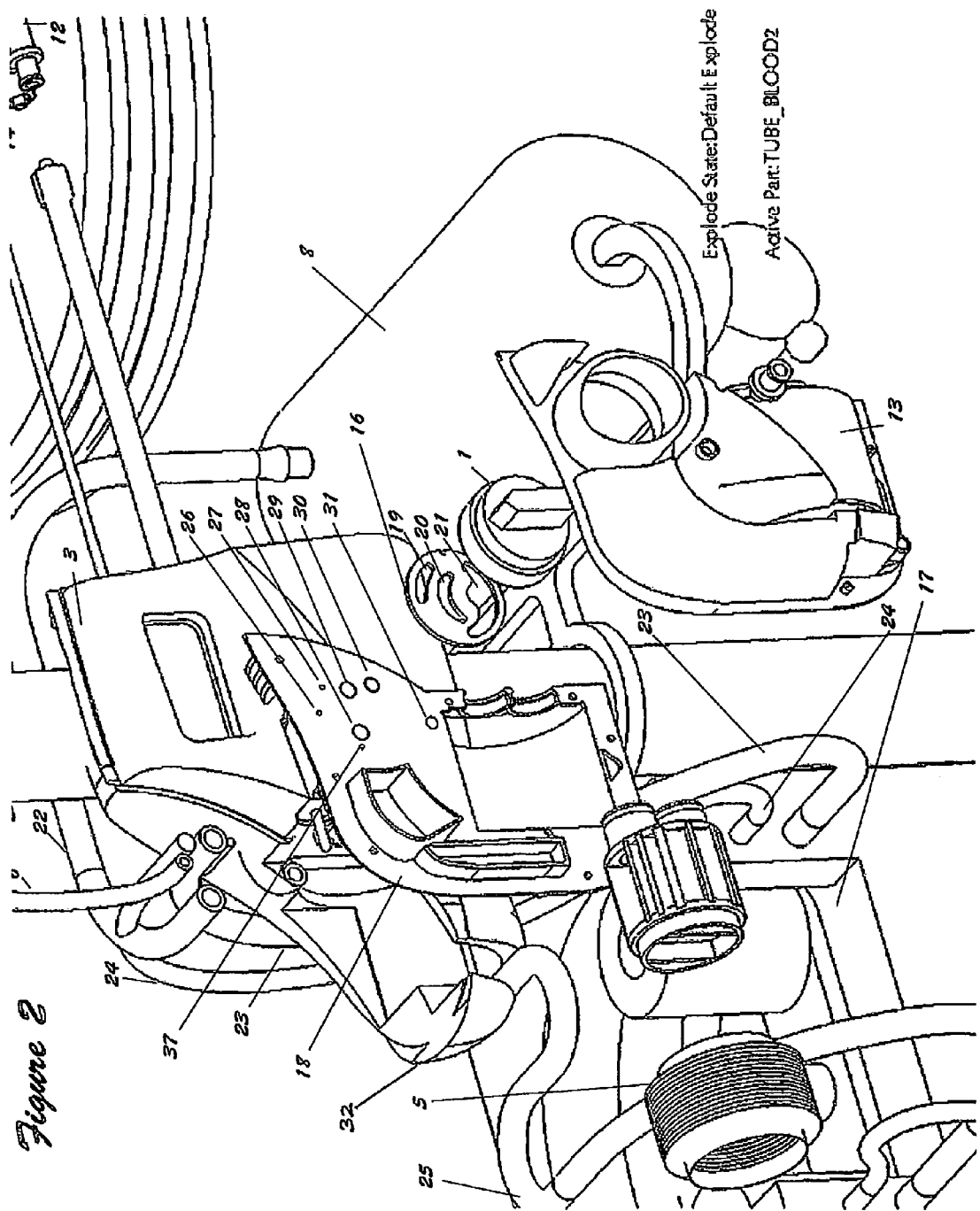
FIG. 2 shows an exploded view of the cardioplegia cartridge. Details of the switch can be seen in this view.
Figure 3:
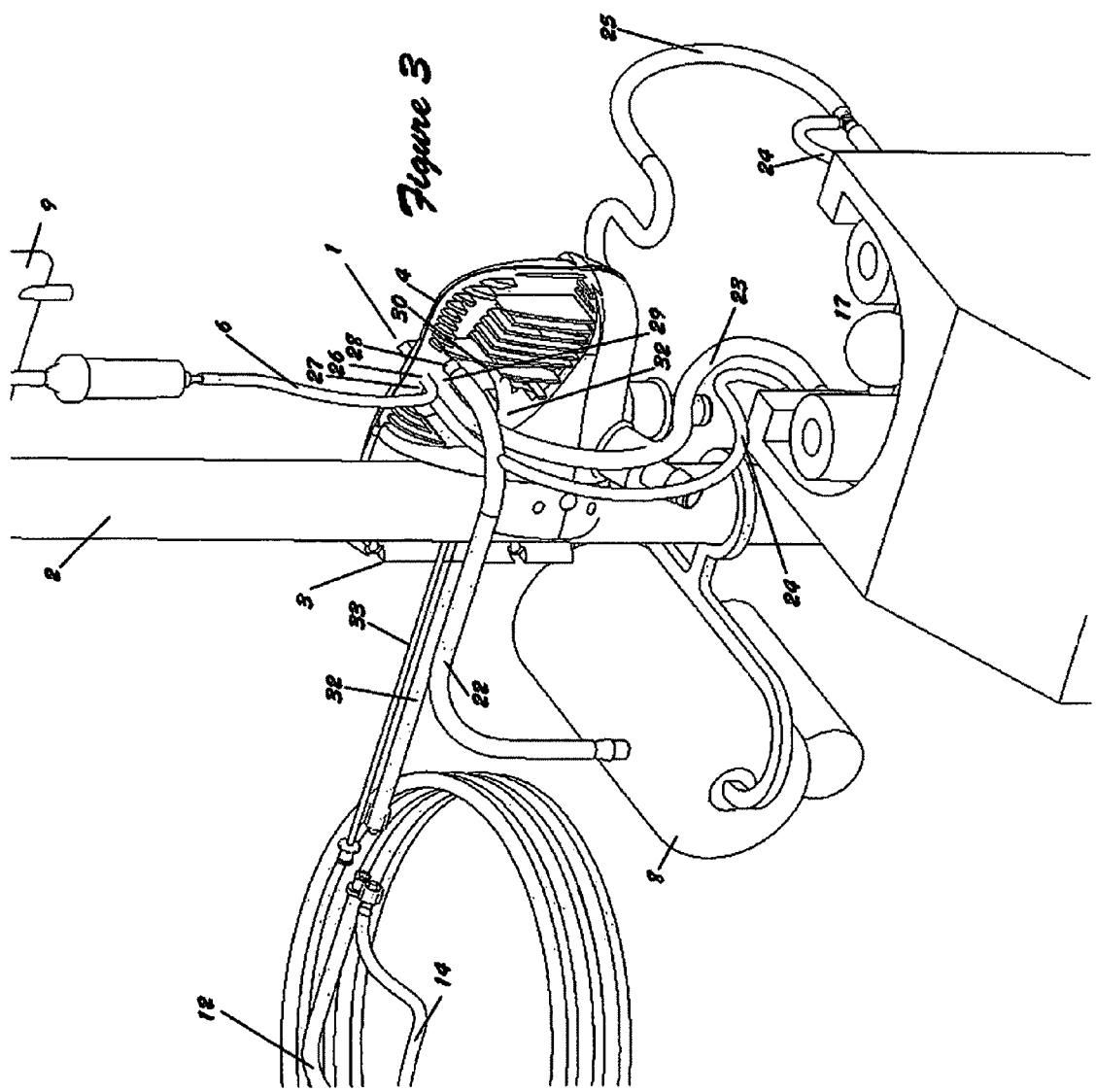
FIG. 3 demonstrates the tubing connections in the rear of the cardioplegia cartridge.

The recirculation switch is illustrated in FIG. 2 which is an exploded view of the cartridge (4). The switch with the knob rotated into the "Delivery mode" is also shown in FIG. 3. The switch is plumbed between the fluid sources (blood oxygenator (8) and cardioplegia drug bag (9) or the recirculation line (14)) and the roller pump (17). The switch will either allow blood and cardioplegia to be pumped to the patient or will circulate the solution through the heat changer, up to the patient and back.

The Recirculation Switch

The rotatable switch is comprised of two mating elements; a manifold (16) and the switch outer body (1). The manifold is made from silicone, polyisoprene, or rubber. Silicone is a thermoset that resists creep and is often used as a gasket material. The two switch elements (1 and 16) are bonded together to form a single rotatable knob assembly with integral manifolds. An alternative version is to mold the knob (1) and gasket (16) in a single silicone part.

The switch assembly is sandwiched between two plastic housings (items 13 and 18 shown in FIG. 2). The plastic housings are welded together to form a compression seal between the rubber manifold (16) and the front and rear housings (18 and 13). The rear housing (18) contains fittings which are molded into the plastic housing and are glued to the plastic tubing. These fittings will be described in the next section. A lubricant such as Nusil MED-360 or MED480 is applied to the silicone gasket to make it easier to rotate the knob.

Molded or formed into the rotating manifold (16) are channels which mate the inlet plastic tubing with the outlet hoses.

Again referring to FIGS. 2 and 3, the manifold (16) has three channels. One of the three manifold channels (20) connects the blood inlet tubing (22) coming from the oxygenator to the tubing (23) going to the roller pump (17). When the switch is rotated into "Delivery" mode, the oxygenator blood source is connected to the pump through this channel (20). Likewise, the second channel (19) connects the drug inlet tubing (6) to the drug tubing (24) routed through the pump raceway. The recirculation channel is blocked by the manifold (16) when the switch is put into "Delivery" mode.

Figure 4:
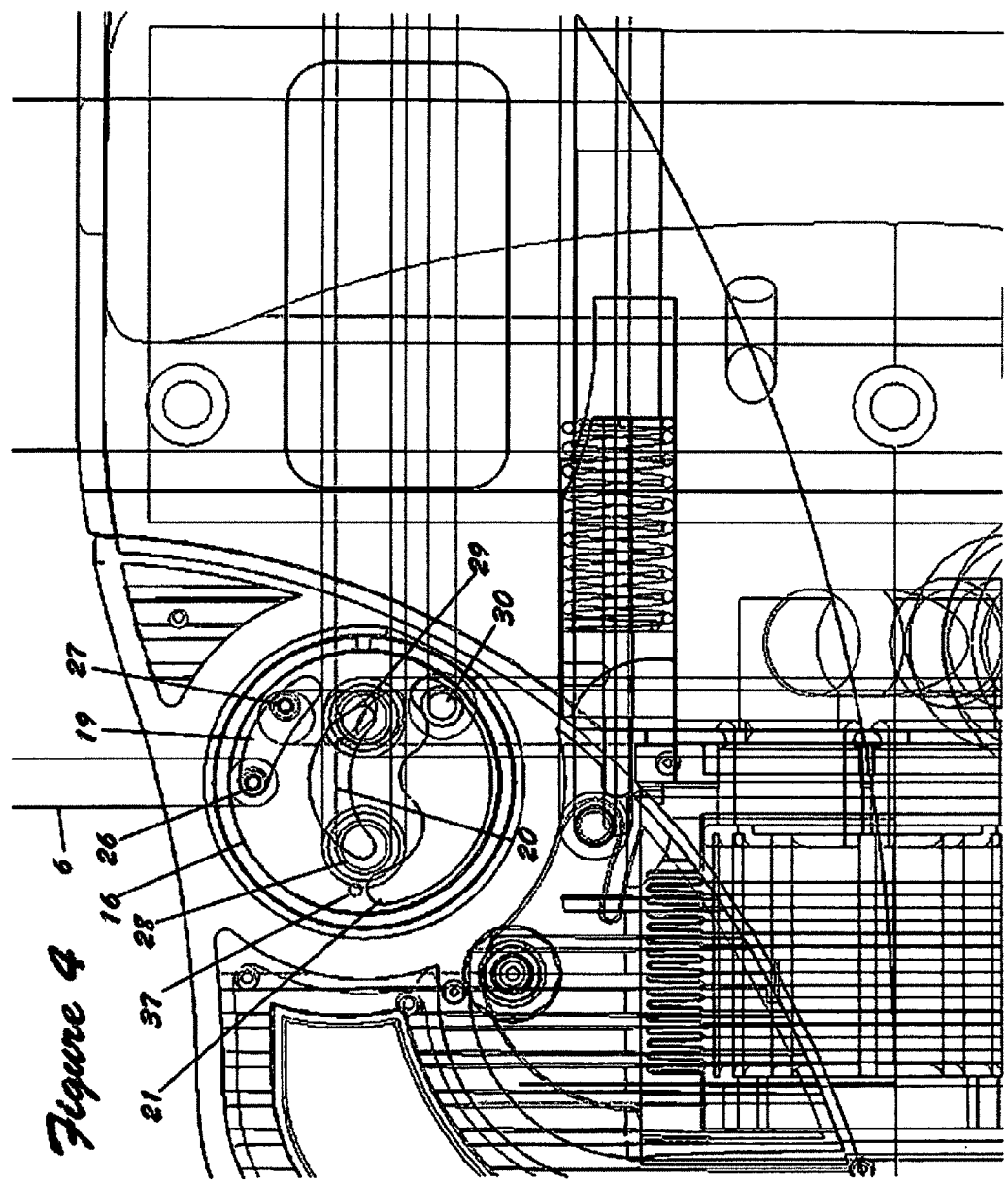
FIG. 4 has a close up view of the switch in delivery mode. This is the orientation used when delivering cardioplegia drug and blood through the pump and into the patient's coronary arteries.

At the cessation of cardioplegia delivery, the perfusionist would turn the cardioplegia pumps speed to a lower flow rate and rotate the switch into the "recirculation" mode which is shown in FIG. 4. FIG. 4 shows the manifold (16) rotated approximately 90 degrees. This would bring the recirculation line (14) in fluid connection with both the hoses connected to the cardioplegia pump (23 and 24). It is important that both pump lines are in fluid communication with the recirculation line so that one line is not blocked. A blocked pump inlet line will generate a negative pressure in that line. If this happens to be a blood line, the negative pressure will lyse the red blood cells since red blood cells are especially fragile in the presence of negative pressure.

Figure 5:
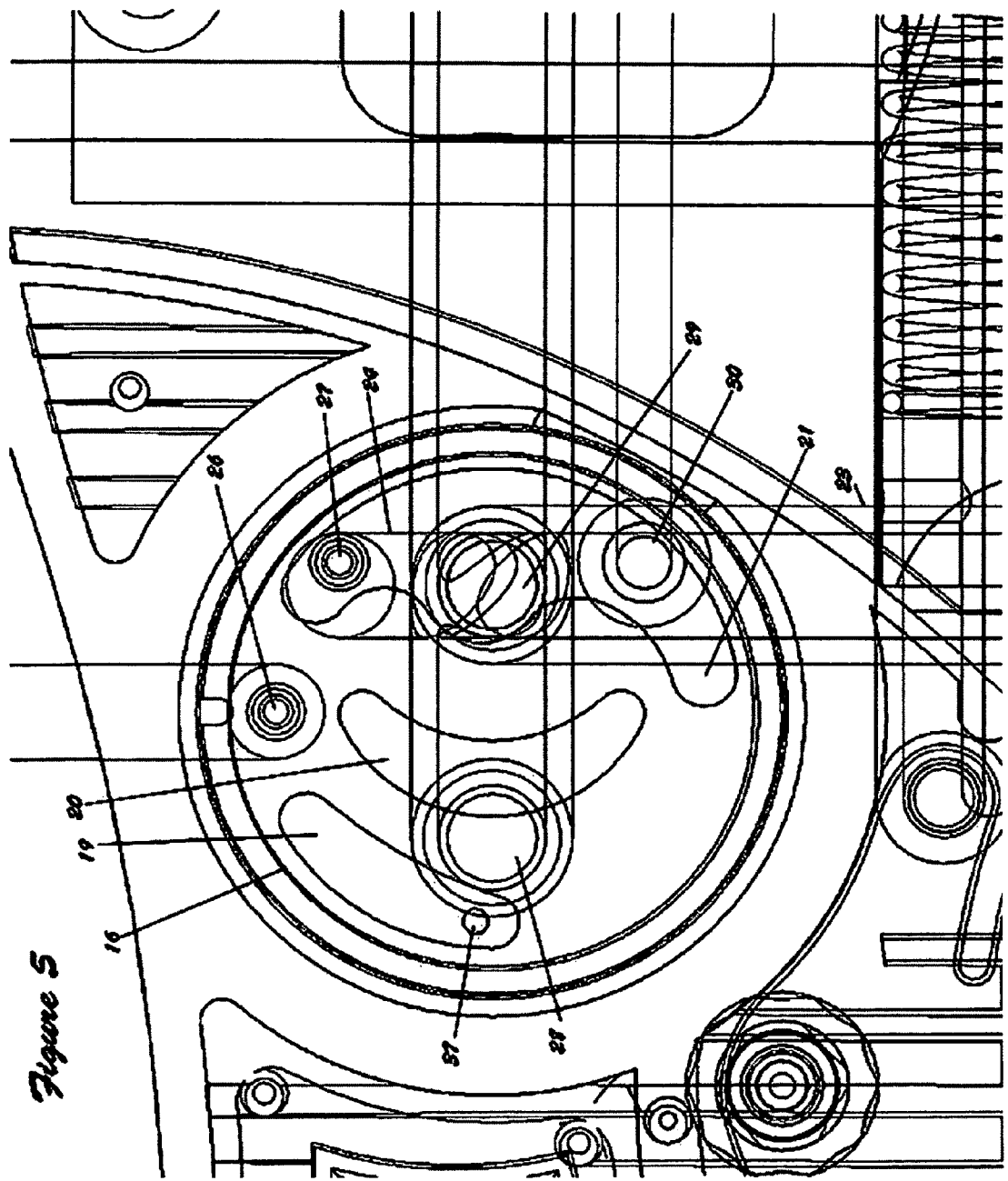
FIG. 5 illustrates the switch in recirculation mode. In this mode the oxygenator and drug bag are disconnected from the pump. Because the volume is closed, the fluid in the circuit is forced to travel up to the Y connector near the patient's heart and back down the recirculation tubing into the pump.
Figure 6:
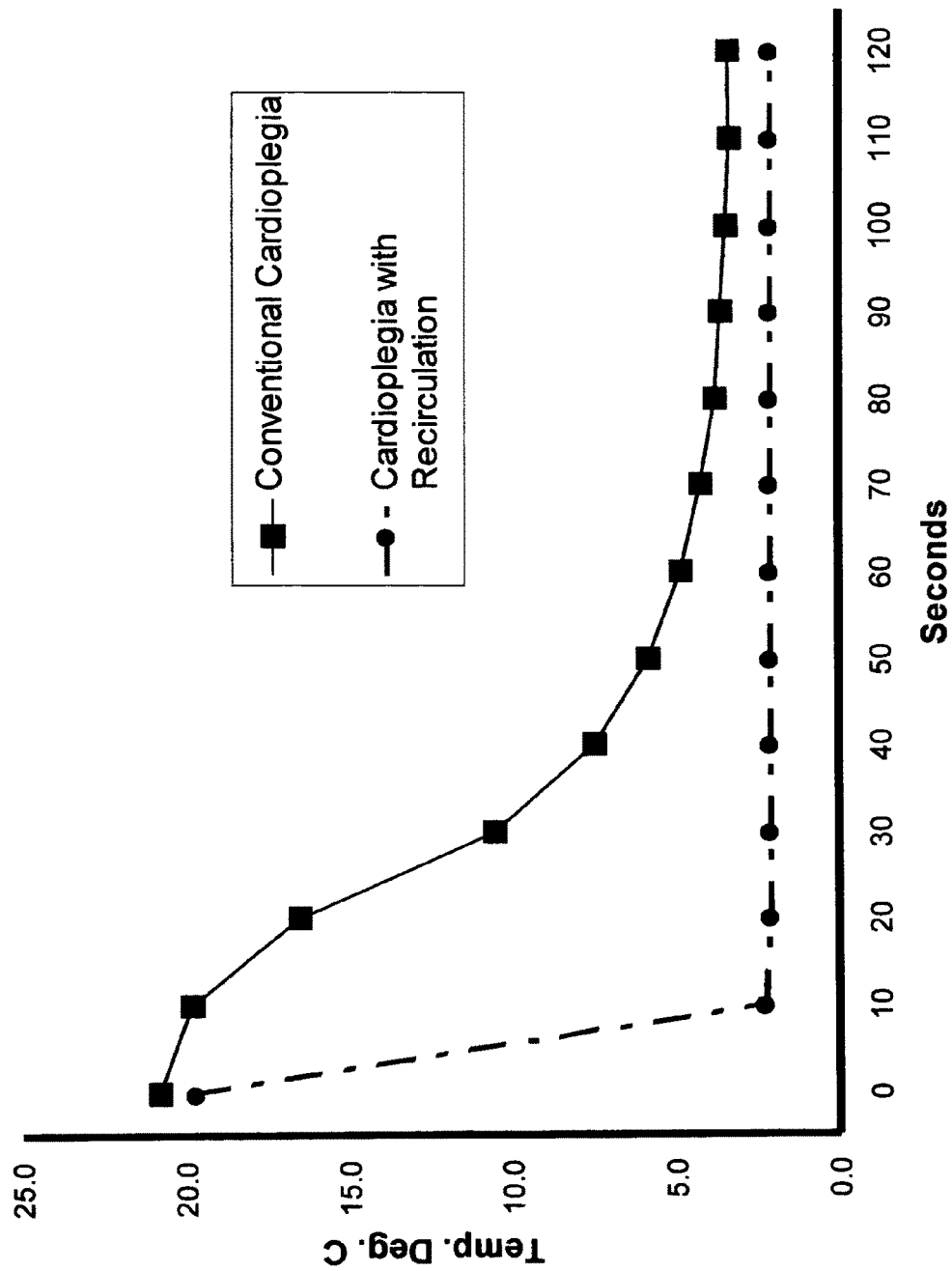
FIG. 6 graphically displays the temperature of the solution entering the patient's heart with a conventional cardioplegia circuit compared to the temperature obtained with the recirculation feature in the current invention. (D0020-003 rev. A: "Solution Temperature-Conventional vs. Recirculation")

FIG. 5 show the recirculation line in fluid communication with both pump lines. In FIG. 5, the blood oxygenator tubing (22) mates with the plastic pump port (28). The blood pump tube (23) connects to a plastic pump port (29). FIG. 5 also demonstrates how the drug inlet port (26) is not in fluid communication with the drug pump port (27). The channel (21) connects the blood pump port (29) and the drug pump port (27) directly with the recirculation port (30). The recirculation port (30) couples to the recirculation line (14).

The two inlet ports (28) and (26) connected to the oxygenator (8) and drug bag (9) respectively are both occluded by the switch manifold (16). Since the volume is closed, only fluid from the recirculation line can be pulled through the switch into the pump. This allows the fluid to recirculates at a slow flow rate during the fifteen or so minutes until the next dose of cardioplegia is required. Following the flow of fluid in recirculation mode, we will arbitrarily start the fluid circuit at the distal "Y" connector (10). The pump tubing ports (27 and 29) are connected directly to the recirculation line fitting (30) through the channel (21) in the switch (16). Fluid in the circuit would flow from the "Y" connector (10) through the recirculation line (14) into channel (21) in the switch manifold (16). The blood/drug mixture would then flow from the channel in the switch (21) through the two pump tubes (23 and 24). Both pump tubes exiting the pump connect at the tee and permit the passage of pressurized fluid through tube (25) into the heat exchanger (5). Fluid exits the heat exchanger (5), passing through the bubble trap (34) out the module to the delivery line (12). Fluid then flows to the "Y" connector (10) thereby completing the circuit. There is no communication of any fluid outside of the disposable cardioplegia circuit. Since the volume is fixed, fresh blood and drug cannot be pulled into the circuit. According to law of conservation of mass, (http://en.wikipedia.org/wiki/conservation_of_mass) no fluid can exit a closed system to be delivered into the patient's coronary arteries. The law of conservation of mass states "that the mass of a closed system will remain constant, regardless of the processes acting inside the system. An equivalent statement is that mass cannot be created/destroyed, although it may be rearranged in space, and changed into different types of particles. This is also the central idea behind the first law of thermodynamics."

During recirculation of the blood drug mixture, the water flow to the blood/water heat exchanger (5) would be continued. This water flow would continue to pump chilled water on one side of the heat exchanger and cooling the recirculating fluid. By continually cooling the blood and cardioplegic drug mixture, the cardioplegia fluid downstream of the heat exchanger remains at very cold (2° C.) temperatures. Immediately upon rotating the switch from "Recirculation" position to "Delivery" position, very cold cardioplegia flows into the coronary arteries of the heart. In delivery mode, fresh blood and drug will be pulled into the circuit forcing the fluid to exit the delivery line into the patient's heart.

Priming the Circuit

Figure 8:
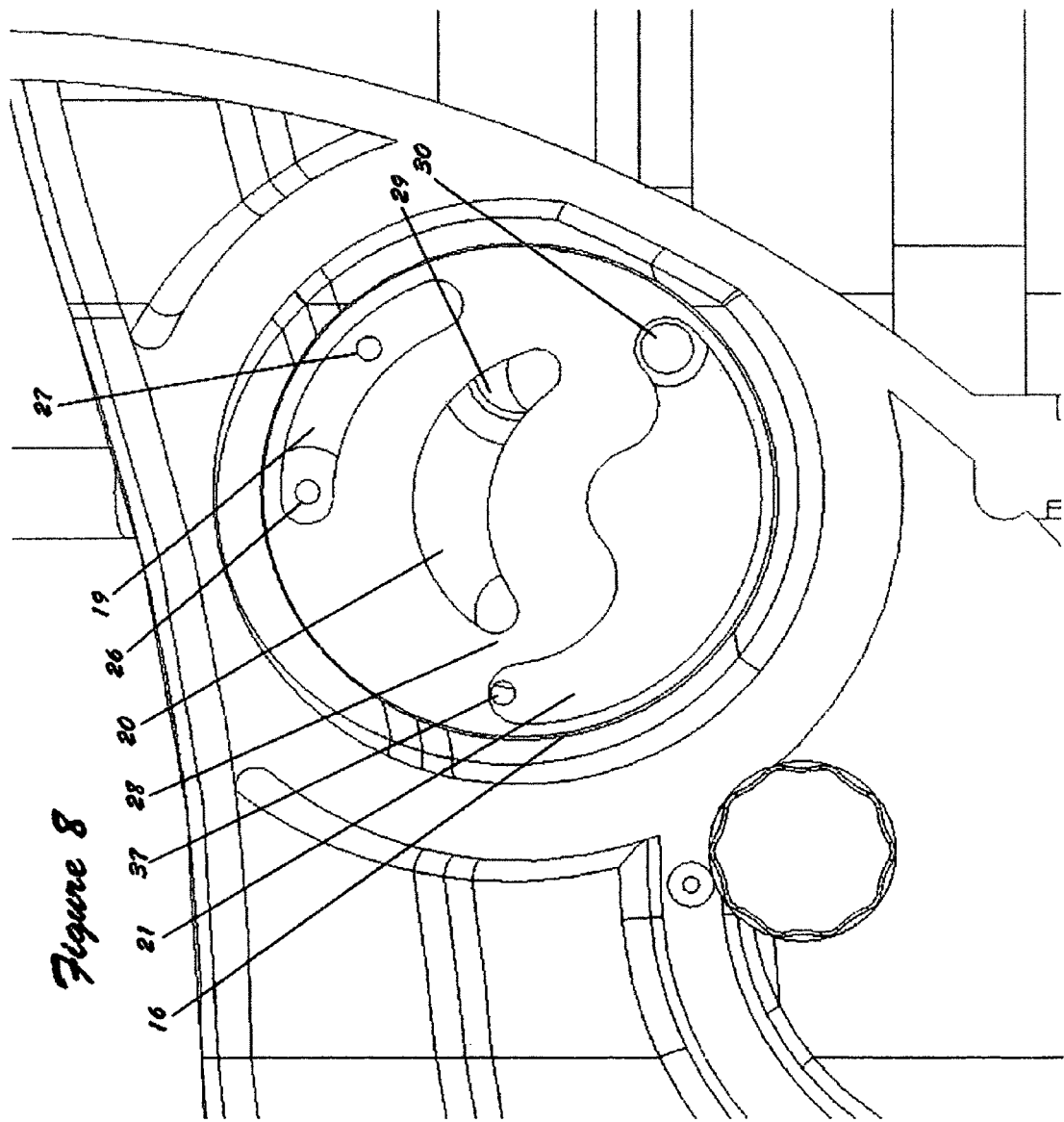
FIG. 8 illustrates the switch in priming mode.

Priming the system requires one additional switch position. To prime the system, the switch is rotated into the position shown in FIG. 8. In this switch position, the recirculation return line is rotated up into a position in which the recirculation inlet port (30) is in fluid communication with a vent hole (37). The hole (37) vents to atmospheric pressure. This fluid path will be explained later in the description of the priming process.

The priming process starts by pumping priming solution from the oxygenator (8) through channel (20) as in the same manner as would be done in delivery mode. Note: the oxygenator circuit would be previously primed with a saline prime fluid and would contain no blood when the cardioplegia set is primed. Refer to both FIGS. 1 and 8 to follow the priming process. Drug is pumped from the drug bag (9) through channel (19) into the drug tube (24). Blood is pumped from the oxygenator through channel (20) into the pump tube (23). The drug and blood prime solution would pass through the roller pump (17) through tubes (23) and (24). The priming solution would combine at the "tee" junction and then flow into the heat exchanger (5) and bubble trap (34) before exiting into the delivery line (12). Once the priming solution is pumped past the distal "Y" connector (10) into the cannula line (11), the pump technician would stop the pump. The pump technician would or a nurse at the operating table would place a hemostatic clamp to fully occlude line the distal cannula line (11). Once the cannula line (11) is clamped, the pump technician would again turn on the pump allowing priming solution to flow down the recirculation tubing (14).

Figure 7:
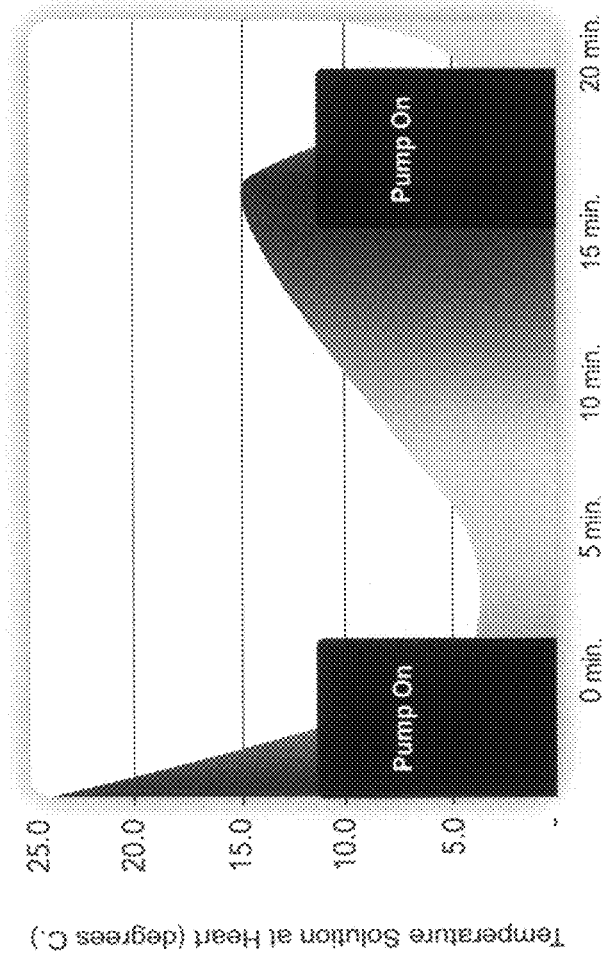
FIG. 7 shows a theoretical graph of solution outlet temperature versus time when cardioplegia is delivered intermittently.

Referring to FIG. 7, once the priming fluid reached the port (30) in the switch, the solution would flow through the recirculation channel (21) in the switch gasket (16). The channel would fill as air was pumped out of the vent hole (37). The perfusionist would be instructed to monitor the switch and vent hole and turn off the pump when priming solution flowed out of the vent hole. At this point the circuit is fully primed and the switch can be rotated back to either delivery or recirculation positions.

REFERENCES CITED

U.S. Patent Documents

| | | |
|---|---|---|
| 3,776,249 | December 1973 | Wailes et al. |
| 3,927,955 | December 1975 | Spinosa et al. |
| 4,011,940 | March 1977 | Neal et al. |
| 4,038,981 | August 1977 | LeFevre et al. |
| 4,105,028 | August 1978 | Sadlier et al. |
| 4,187,057 | February 1980 | Xanthopoulos |
| 4,249,923 | February 1981 | Walda |
| 4,256,437 | March 1981 | Brown |
| 4,259,985 | April 1981 | Bergmann |
| 4,333,486 | June 1982 | Ciccozzi |
| 4,372,304 | February 1983 | Avakian et al. |
| 4,425,113 | January 1984 | Bilstad |
| 4,425,116 | January 1984 | Bilstad et al. |
| 4,427,009 | January 1984 | Wells |
| 4,512,163 | April 1985 | Wells |
| 4,433,971 | February 1984 | Lindsay |
| 4,445,826 | May 1984 | Tarr |
| 4,493,710 | January 1985 | King et al. |
| 4,496,133 | January 1985 | Sule |
| 4,512,764 | April 1985 | Wunsch |
| 4,524,802 | June 1985 | Lawrence et al. |
| 4,526,515 | July 1985 | DeVries |
| 4,537,561 | August 1985 | Xanthopoulos |
| 4,559,036 | December 1985 | Wunsch |
| 4,626,241 | December 1986 | Campbell et al. |
| 4,637,813 | January 1987 | DeVries |
| 4,651,898 | March 1987 | Bell |
| 4,673,389 | June 1987 | Archibald et al. |
| 4,681,563 | July 1987 | Deckert et al. |
| 4,713,051 | December 1987 | Steppe et al. |
| 4,714,463 | December 1987 | Archibald et al. |
| 4,735,558 | April 1988 | Kienholz et al. |
| 4,793,589 | December 1988 | Eldredge et al. |
| 4,798,580 | January 1989 | DeMeo et al. |
| 4,830,581 | May 1989 | Hendriks |
| 4,842,584 | June 1989 | Pastrone |
| 4,846,177 | July 1989 | Leonard |
| 4,874,359 | October 1989 | White et al. |
| 4,887,636 | December 1989 | Rothen |
| 4,888,004 | December 1989 | Williamson, IV et al. |
| 4,889,148 | December 1989 | Smazik |
| 4,925,444 | May 1990 | Orkin et al. |
| 4,993,594 | February 1991 | Becker et al. |
| 4,998,914 | March 1991 | Wiest et al. |
| 5,044,902 | September 1991 | Malbec |
| 5,057,278 | October 1991 | Maxwell et al. |
| 5,094,260 | March 1992 | Stuart et al. |
| 5,094,820 | March 1992 | Maxwell et al. |
| 5,125,891 | June 1992 | Hossain et al. |
| 5,154,693 | October 1992 | East et al. |
| 5,181,842 | January 1993 | Sunderland et al. |
| 5,195,960 | March 1993 | Hossain et al. |
| 5,199,604 | April 1993 | Palmer et al. |
| 5,207,642 | May 1993 | Orkin et al. |
| 5,267,956 | December 1993 | Beuchat |
| 5,304,126 | April 1994 | Epstein et al. |
| 5,306,242 | April 1994 | Joyce et al. |
| 5,318,515 | June 1994 | Wilk |
| 5,320,502 | June 1994 | Davis |

-continued

U.S. Patent Documents

| | | |
|---|---|---|
| 5,328,057 | July 1994 | Hellenberg et al. |
| 5,350,083 | September 1994 | Du |
| 5,358,481 | October 1994 | Todd et al. |
| 5,385,540 | January 1995 | Abbott et al. |
| 5,403,277 | April 1995 | Dodge et al. |
| 5,403,281 | April 1995 | O'Neill et al. |
| 5,464,388 | November 1995 | Merte, et al. |

Foreign Patent Documents

| | | |
|---|---|---|
| 0362822 | April, 1990 | EP |
| 0529902 | March, 1993 | EP |
| WO91/15149 | October, 1991 | WO |
| WO93/19791 | October, 1993 | WO |

D0020-003 "Solution Outlet Temperature—Conventional vs. Recirculation" Internal company report.

Medtronic DLP On Line Catalog http://www.medtronic.com/cardsurgery/arrested_heart/cannulae.html

What is claimed is:

1. A delivery system for alternating the source to a pump either from external fluid sources or from an internal recirculation loop, the system comprising:
   a first supply port and a second supply port which are connected through flexible tubes to two independent external fluid sources;
   a third port and a fourth ports connected to two separate pump tubes;
   a fifth port connected to a recirculation tube
   a sixth port vented to atmospheric pressure;
   and a manifold containing a first channel, a second channel and a third channel, wherein the manifold is rotatable between at least a first manifold switch position and a second manifold position;
   wherein rotating the manifold into the first manifold switch position orients the first channel to provide fluid communication between the first supply port and the third port leading to the pump and orients the second channel to provide fluid communication between the second fluid port and the fourth pump port, wherein the third channel is only in fluid communication with the fifth recirculation port;
   wherein rotating the manifold into the second manifold switch position orients the first and the second channels to occlude flow and positions the third channel to provide fluid communication between the fifth port and the third port and the fourth port leading to the pump.

2. The delivery system described in claim 1 in which the switch is contained in a cartridge with a heat exchanger, pressure and temperature sensor and a bubble trap.

3. The delivery system described in claim 1 in which the switch is contained in a cartridge containing a heat exchanger, pressure and temperature sensor and a bubble trap in which water inlet lines are automatically connected when the cartridge is installed into the bracket.

4. The delivery system described in claim 1 in which the switch is contained in a cartridge containing a heat exchanger, pressure and temperature sensor and a bubble trap in which the temperature sensor is automatically engaged when the cartridge is installed in the bracket.

5. A delivery system for alternating the source to a pump either from external fluid sources or from an internal recirculation loop, the system comprising:
- a first supply port and a second supply port which are connected through flexible tubes to two independent external fluid sources;
- a third port and a fourth ports connected to two separate pump tubes;
- a fifth port connected to a recirculation tube;
- a sixth port vented to atmospheric pressure;
- and a manifold containing distinct a first channel, a second channel and a third channel, wherein the manifold is rotatable between at least a first manifold switch position and a third manifold position;
- wherein rotating the manifold into the first manifold switch position orients the first channel to provide fluid communication between the first supply port and the third port leading to the pump and orients the second channel to provide fluid communication between the second fluid port and the fourth pump port, wherein the third channel is only in fluid communication with the fifth recirculation port;
- wherein rotating the manifold into the third manifold switch position orients the first channel to provide fluid communication between the first supply port and the third port leading to the pump, and orients the second channel to provide fluid communication between the second fluid port and the fourth pump port, and orients the third channel to provide fluid communication between the fifth recirculation port and the sixth port, wherein the sixth port is vented to atmospheric pressure so as to facilitate complete priming of the switch.

* * * * *